US010687769B2

(12) United States Patent
Beckhaus

(10) Patent No.: US 10,687,769 B2
(45) Date of Patent: Jun. 23, 2020

(54) METHOD FOR CREATING A 3D DENTAL X-RAY IMAGE

(71) Applicant: DENTSPLY SIRONA Inc., York, PA (US)

(72) Inventor: Christian Beckhaus, Darmstadt (DE)

(73) Assignee: DENTSPLY SIRONA Inc., York, PA (US)

( * ) Notice: Subject to any disclaimer, the term of this patent is extended or adjusted under 35 U.S.C. 154(b) by 30 days.

(21) Appl. No.: 15/748,655

(22) PCT Filed: Aug. 5, 2016

(86) PCT No.: PCT/EP2016/068718
§ 371 (c)(1),
(2) Date: Jan. 30, 2018

(87) PCT Pub. No.: WO2017/021520
PCT Pub. Date: Feb. 9, 2017

(65) Prior Publication Data
US 2018/0220978 A1    Aug. 9, 2018

(30) Foreign Application Priority Data

Aug. 6, 2015 (DE) .................. 10 2015 215 048

(51) Int. Cl.
*A61B 6/04* (2006.01)
*A61B 6/03* (2006.01)
(Continued)

(52) U.S. Cl.
CPC ................ *A61B 6/14* (2013.01); *A61B 6/032* (2013.01); *A61B 6/04* (2013.01); *A61B 6/08* (2013.01); *A61B 6/5211* (2013.01)

(58) Field of Classification Search
CPC .. A61B 6/032; A61B 6/04; A61B 6/08; A61B 6/14; A61B 6/5211
See application file for complete search history.

(56) References Cited

U.S. PATENT DOCUMENTS 7,787,586 B2  8/2010  Yoshimura et al.
8,750,450 B2  6/2014  Ulrici et al.
(Continued)

FOREIGN PATENT DOCUMENTS

DE       19962205 A1    7/2001
DE       102008010537 A1  8/2008
DE       102008035412 A1  2/2010

OTHER PUBLICATIONS

International Search Report and Written Opinion of International Application No. PCT/EP2016/068718 dated Nov. 22, 2016 (English translation).
(Continued)

*Primary Examiner* — Mark R Gaworecki
(74) *Attorney, Agent, or Firm* — Dentsply Sirona Inc.

(57) ABSTRACT

Disclosed herein is a method for creating a 3D dental X-ray image of a jaw region of a patient from a plurality of projection exposures of an exposure volume having a cylindrical core volume with a flat base area, generated during a circulation of an X-ray emitter and an X-ray detector about the head of the patient. The patient may be positioned relative to the core volume so that the jaw region is located within the core volume, and where a bottom edge of the lower jaw of the patient and the base area of the core volume are aligned at least approximately parallel.

7 Claims, 1 Drawing Sheet

(51) Int. Cl.
*A61B 6/08* (2006.01)
*A61B 6/14* (2006.01)
*A61B 6/00* (2006.01)

(56) References Cited

U.S. PATENT DOCUMENTS

2003/0058988 A1 3/2003 Molteni et al.
2008/0232540 A1 9/2008 Yoshimura et al.
2011/0129058 A1 6/2011 Ulrici et al.

OTHER PUBLICATIONS

International Preliminary Report on Patentability of International Application No. PCT/EP2016/068718 dated Feb. 6, 2018 (English translation).

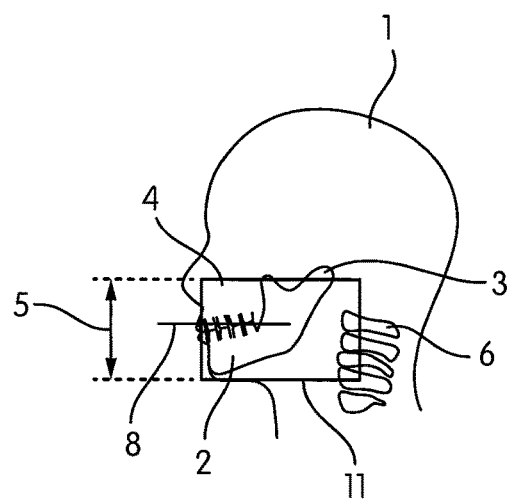
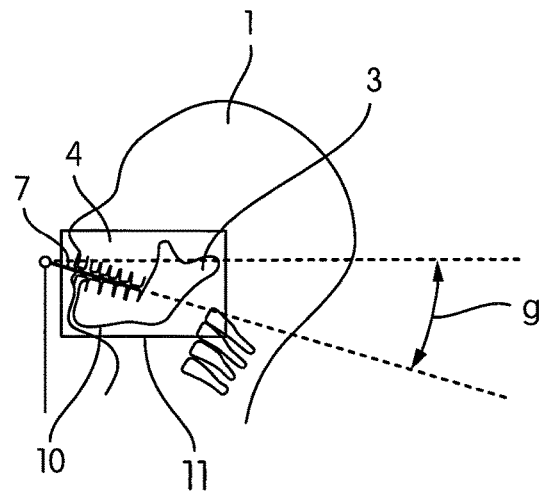
FIG. 1A          FIG. 1B
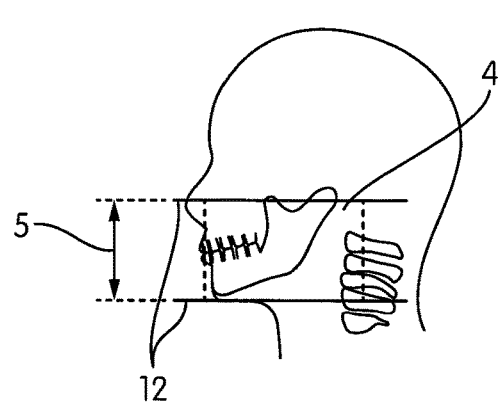
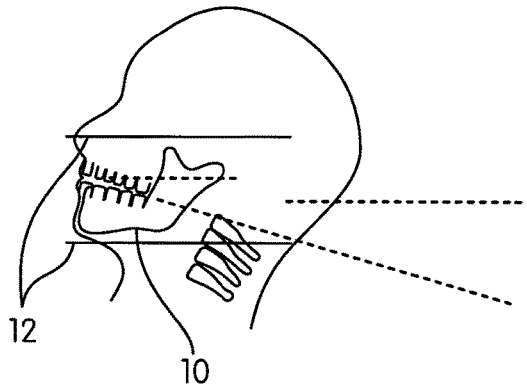
FIG. 2A          FIG. 2B

METHOD FOR CREATING A 3D DENTAL X-RAY IMAGE

TECHNICAL FIELD

The invention relates to a method for creating a 3D dental X-ray image of a jaw region of a patient from a plurality of projection exposures of an exposure volume having a cylindrical core volume with a flat base area, generated during a circulation of an X-ray emitter and an X-ray detector about the head of the patient, wherein the patient is positioned so that the jaw region is located within the core volume.

BACKGROUND INFORMATION

In known dental X-ray devices for creating images in the jaw or head region of a patient, the patient is positioned prone, standing, or seated. For positioning, for example, a bite piece or a forehead support is used.

For example, a method and a device for generating a 3D X-ray image are known from DE 10 2008 035 412 A1, wherein a patient is positioned by means of a bite piece between an X-ray emitter and an X-ray detector, and the X-ray image is generated by a circulation of the X-ray emitter and X-ray detector around the positioned patient.

The exposure volume of such a device is approximately cylindrical with a horizontally extending base area. The size, in particular the height, depends essentially on the size or height of the detector and the X-ray beam, and must be adjusted to the size of the object to be imaged, thus the size of a human jawbone.

The object consists in refining the method known from the prior art and in particular enabling a most optimal use of the exposure volume or a reduction of the necessary exposure volume for depicting the complete jaw area including the jaw joint.

SUMMARY OF THE INVENTION

The subject matter of the invention is a method for creating a 3D dental X-ray image of a jaw region of a patient from a plurality of projection exposures of an exposure volume having a cylindrical core volume with a flat base area, generated during a circulation of an X-ray emitter and an X-ray detector about the head of the patient, wherein the patient is positioned so that the jaw region is located within the core volume, and a bottom edge of a lower jaw of the patient and the base area of the core volume are aligned at least approximately parallel to one another.

A typical X-ray device for generating a 3D dental image has an exposure volume scanned during the circulation of X-ray detector and X-ray emitter. The shape of the exposure volume is determined by the circulation path of detector and emitter and by the, for example, funnel shape and alignment of the X-ray beam. This may, for example, lead to a so-called 100% exposure volume with a height increasing in the direction of a center, e.g. a cylindrical volume with cones applied on one side or both sides. The exposure volume may, however, have any other form of the exposure volume depending on the X-ray device used, e.g., spherical, ellipsoid, conical, etc.

To measure the jaw region of a patient, the jaw region must be positioned within the exposure volume. To keep the radiation load as low as possible, the size of the exposure volume should not particularly exceed the size of the jaw region, even if the shape of the exposure volume naturally does not correspond to the form of the volume which the jaw region occupies.

Core volume designates a partial volume of this exposure volume, which on the one hand lies completely within the exposure volume, thus may and should be used for measuring, and on the other hand is cylindrically shaped, wherein the base area of the core volume is aligned at least approximately perpendicular to the axis or axes of rotation of the X-ray detector or of the X-ray emitter, and functions as a reference for aligning the patient. It should be noted that the core volume has the general shape of a cylinder, which has a flat base area, a cover area corresponding to the base area displaced along a straight line relative to the base area, and a straight lateral surface connecting these to areas. The core volume must be large enough that it covers the entire region to be imaged, thus, for example, the entire jaw region. It is understood that the exposure volume is ideally not much larger than the core volume, and the core volume corresponds in the ideal case at least theoretically exactly to the part of the exposure volume of the X-ray device reliably usable for the measurement.

X-ray devices, whose emitters and detectors rotate about a vertical axis, have a core volume with a base area extending at least approximately horizontal. The patient is positioned sitting or standing between the X-ray emitter and X-ray detector.

Other X-ray devices enable a prone position of the patient, whereby the emitter and detector correspondingly circle about an at least approximately horizontal axis, and the base area of the cylindrical core volume extends at least approximately vertically.

In a normal, straight head pose of a standing or sitting patient, the bottom edge of the lower jaw extends at a slight slant from chin to the back of the head, while the occlusal plane extends essentially horizontally. If the neck is overextended, thus bent backward, then the bottom edge of the lower jaw may be aligned parallel to a horizontal plane, while the occlusal plane extends obliquely.

An alignment of the bottom edge of the lower jaw parallel to the base area of the core volume, which is achieved by overextending the head, enables an optimal use of the core volume, since the jaw region assumes a volume in an overextended head pose which particularly approximates a cylindrical volume with a horizontal base area.

One advantage of this positioning is that the height of the core volume may be kept low and despite this the entire jaw region with the jaw joint and optionally also the maxillary sinus may be accommodated. Furthermore, the jaw region is positioned in the core volume by such an alignment that the accommodation of additional, potentially interrupting structures, like the cervical spinal column, may be largely avoided. Furthermore, this positioning achieves that the organs particularly sensitive to radiation, eyes and thyroid, lie farthest outside of the irradiated volume, by which means the effective dosage of an exposure is significantly reduced.

Advantageously, a first angle of an occlusal plane and/or a jaw joint of the patient positioned relative to the base area or a lateral surface of the core volume is determined and a positional correction of the 3D X-ray exposure about the first angle is carried out. Since the occlusal plane, thus the bite surface in a normal head position of a standing or seated patient extends essentially horizontal, the first angle between the occlusal plane of a positioned patient to a horizontally extending base area of an X-ray device conceived of for standing or seated positioning provides the deviation of the position of the patient from the normal head position. This correspondingly applies for a prone positioning and a base area of the core volume extending vertically. By undertaking a positional correction about the first angle, the 3D X-ray exposure may be depicted in a normal head position. Thus, despite an overextended positioning of the head during the exposure, a familiar view of the jaw may be provided in the 3D X-ray image obtained. This positional correction may be carried out directly at or during the reconstruction, or also only subsequent thereto for the depiction of the reconstructed data in a display program.

Advantageously, a first angle of an occlusal plane and/or a jaw joint of the position patient relative to the base area or a lateral surface of the core volume is determined and a positional correction of the 3D X-ray exposure about a second angle is carried out, which has a fixed difference to the first angle. If there exists particular interest in a subregion of the jaw region to be measured, e.g., the top of the palate or the sinus floor, then this may be taken into account by an offset during the positional correction so that the depicted data of an exposure correspond to a head bent slightly forward or backward.

Advantageously, a mechanical positioning means, in particular a bite piece and/or a forehead support and/or a chin support and/or a support for the nasal root is used for the positioning. Every known positioning means may be used as the positioning means. A bite piece is, for example, a mechanical positioning means, which has a range in the mouth to be assumed by a patient. This may, for example, be an occlusal bite piece. The bite piece enables both a simple positioning and also a simple determination of the angle of deviation from a normal head position.

Advantageously, a light- or laser range indicator is used for positioning. The positioning of the patient may also be checked or carried out easily and comfortably for the patent by means of a light- or laser range indicator, thus the laser lines projected on the patient head.

The determination of the angle of the deviation from a normal head position may, e.g., be carried out using a statistical average value obtained from a lot of exposure data or a determination of the occlusal plane in the reconstructed data set with the aid of suitable algorithms, like segmentation of the mastication surfaces.

Advantageously, the light- or laser range indicator is a light- or laser sight.

BRIEF DESCRIPTION OF THE DRAWINGS

Embodiments of the invention are depicted in the drawings. As shown in:

FIGS. 1A, B the positioning of a patient by means of a bite piece, and

FIGS. 2A, B the positioning of a patient by means of a laser range indicator.

DETAILED DESCRIPTION OF THE INVENTION

FIG. 1A schematically shows a patient head 1 in a natural head position in which a lower jaw 2 and a jaw joint 3 are sketched out. A cylindrical core volume 4 of an exposure volume (not shown) having a height 5 and a base area 11 is depicted by lateral demarcation lines and covers lower jaw 2 at least partially. An occlusal plane 8 of lower jaw 2 extends approximately parallel to base area 11 of core volume 4.

In order to accommodate entire lower jaw 2, in particular also jaw joint 3 and preferably also an upper jaw (not shown), core volume 4 must be increased in this depicted head position or head alignment. Depending of the size or depth of core volume 4, however, other structures are also included which may interfere with the image quality of the 3D X-ray image or are particularly sensitive to X-ray radiation. As sketched in FIG. 1A, a part of cervical spine 6 is included in a natural head position and a depth of core volume 4 that is too large.

In FIG. 1B, head 1 of the patient is brought from the natural head position into an overextended position. For this purpose, a bite piece 7 may be used, as depicted in FIG. 1B, which aligns occlusal plane 8 in a first angle 9 to base area 11. First angle 9 is adjusted so that a bottom edge 10 of lower jaw 2 is aligned mostly parallel to base area 11 of cylindrical core volume 4. A height of bite piece 7 is adjusted so that bottom edge 10 is positioned at the height of base area 11 or somewhat higher.

In this overextended position of head 1, core volume 4 suffices to detect the entire jaw area of upper jaw (not shown), lower jaw 2 and jaw joint 3. An increase with respect to height 5 is not necessary. This enables the radiation load to be kept low for the patient. Furthermore, the recording of interrupting structures, e.g., the cervical spinal column, may be prevented by the positioning according to the invention. Low demands on maximum height 5 of core volume 4 and correspondingly of the entire exposure volume also enable the use of a more cost effective imaging device or lower production costs for X-ray emitters and detectors (not shown).

In FIGS. 2A and 2B, the positioning of patient head 1 by means of a laser range indicator 12 is indicated. For the positioning by means of a laser or another light source (not shown), for example, by means of a light or laser sight as a laser range indicator 12, two lines are projected on patient head 1 which indicate height 5, the course of base area 11, and the spatial position of core volume 4 (indicated by dashed lines). Patient head 1 is aligned so that bottom edge 10 of lower jaw 2 extends approximately parallel to the lower line of laser range indicator 12.

As a further assistance for the positioning, another line may be projected extending in the middle between the two lines, which should extend from a lip gap of the patient to an auditory channel of the patient in an optimal matching of position and size of the lower jaw to be imaged and the core volume.

REFERENCES

1 Patient head
2 Lower jaw
3 Jaw joint
4 Core volume
5 Height of the core volume
6 Cervical spinal column
7 Bite piece
8 Occlusal plane
9 First angle
10 Bottom edge of the lower jaw
11 Base area of the core volume
12 Laser range indicator

The invention claimed is:

1. A method for creating a 3D dental X-ray image of a jaw region of a patient from a plurality of projection exposures of an exposure volume having a cylindrical core volume with a flat base area, generated during a circulation of an X-ray emitter and an X-ray detector about a head of the patient, wherein the patient is positioned relative to the core volume so that the jaw region is located within the core volume, wherein a bottom edge of a lower jaw of the patient and the base area of the core volume are aligned at least approximately parallel.

2. The method according to claim 1, wherein a first angle of an occlusal plane or of a jaw joint of the patient positioned relative to the base area or a lateral surface of the core volume is determined and a positional correction of a 3D X-ray exposure about the first angle is carried out.

3. The method according to claim 1, wherein a first angle of an occlusal plane or of a jaw joint of the patient positioned relative to the base area or a lateral surface of the core volume is determined and a positional correction of a 3D X-ray exposure about a second angle is carried out, which has a fixed difference to the first angle.

4. The method according to claim 1, wherein a mechanical positioning means is used for positioning.

5. The method according to claim 4, wherein the mechanical positioning means is a bite piece and/or a forehead support and/or a chin support and/or a support for the nasal root.

6. The method according to claim 1, wherein a light- or laser range indicator is used for the positioning.

7. The method according to claim 6, wherein the light- or laser range indicator comprises a light or laser sight.

* * * * *